United States Patent [19]

Lipp et al.

[11] Patent Number: 4,668,818

[45] Date of Patent: May 26, 1987

[54] METHYL METHACRYLATE PRODUCTION

[75] Inventors: Hayden I. Lipp, Germantown, Tenn.; Richard H. Squire, Elksview, W. Va.

[73] Assignee: E. I. Du Pont de Nemours and Company, Wilmington, Del.

[21] Appl. No.: 746,073

[22] Filed: Jun. 18, 1985

[51] Int. Cl.$^4$ .................. C07C 67/20; C07C 67/62
[52] U.S. Cl. ..................... 560/215; 560/218
[58] Field of Search ............... 560/215, 218

[56] References Cited

U.S. PATENT DOCUMENTS

| | | | |
|---|---|---|---|
| 2,042,458 | 6/1936 | Crawford | 560/215 |
| 2,816,135 | 12/1957 | Healy | 560/215 |
| 2,890,101 | 6/1959 | Borrell et al. | 560/205 |
| 2,917,538 | 12/1959 | Carlyle | 560/205 |

OTHER PUBLICATIONS

Hiramoto, Hiroo et al., *Chemical Abstracts* vol. 82 (1975) #140,729n.

Chernysheva, R. I. et al., *Chemical Abstracts* vol. 89 (1978) #90, 616v.

*Primary Examiner*—Natalie Trousof
*Assistant Examiner*—L. Hendriksen

[57] ABSTRACT

In the process for the preparation of methyl methacrylate, the addition of aromatic diamine in an acidic environment reduces yellow color in the polymerized product.

7 Claims, No Drawings

METHYL METHACRYLATE PRODUCTION

BACKGROUND OF THE INVENTION

Methyl methacrylate is widely used as a monomer or comonomer in the preparation of shaped objects of polymethyl methacrylate such as sheet stock. Such polymethyl methacrylate sheeting is often used for glazing applications, and the clarity and color of the material is therefore important. Yellowness of the cast sheet is a common problem, and many solutions have been suggested to minimize or eliminate yellow color in the final product. At the same time, the elimination of the color must be done without depreciation of the physical properties of the sheeting or its clarity.

SUMMARY OF THE INVENTION

The instant invention is based on the discovery that a major factor in the yellowness of polymethyl methacrylate sheeting is the production, in the preparation of methyl methacrylate monomer, of biacetyl byproduct of the formula

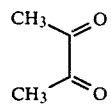

and that this impurity can be eliminated by the introduction of certain diamines.

Specifically, the invention provides, in the process for producing methyl methacrylate monomer by reacting acetone cyanohydrin with sulfuric acid to form methacrylamide and esterifying the methacrylamide with methanol to form methyl methacrylate, the improvement which comprises adding to the reaction mixture an effective amount of hydrazine or aromatic ortho-diamine in the presence of about from 0.1 to 65 weight percent acid catalyst.

DETAILED DESCRIPTION OF THE INVENTION

In the general process to which the present relates, acetone cyanohydrin is used which is generally produced by reacting hydrogen cyanide and acetone in the presence of an alkaline catalyst according to well-known techniques. The acetone cyanohydrin is then reacted with sulfuric acid or oleum to form methacrylamide which, in turn, is reacted in the presence of water with methanol to form methyl methacrylate. One such process is described, for example, in British Pat. No. 1,184,746, hereby incorporated by reference.

In a preferred method for carrying out the amidation reaction in which methacrylamide is formed, appropriate quantities of sulfuric acid or oleum and acetone cyanohydrin are admixed in one or more reaction vessels. The admixing temperature is preferably below 120° C. The final weight ratio of acid to acetone cyanohydrin of is preferably about from 1.3 to 1.8. Ratios of acid below 1.3 result in low yield of the methacrylamide, while acid ratios greater than 1.8 provide little additional benefit.

After mixing, the reactants are heated to a temperature of about from 120° to 150° C. for about from 3 to 25 minutes. The resulting methacrylamide is then either isolated before esterification or preferably reacted directly in the presence of water with methanol to form methyl methacrylate, which is removed by distillation. Unreacted methanol can be removed for recycle to the esterification reaction, while wet methyl methacrylate can be fed to a separate purification column for removal of unreacted methanol and water.

In accordance with the present invention, hydrazine or an aromatic diamine is added to the reaction medium in the preparation of the methyl methacrylate. Representative diamines include, for example, hydrazine, ortho-phenylene diamine of the formula

and ortho-diamino naphthalene. Higher homologs of these compounds can also be used, including, for example, 2,3-diaminophenazine or

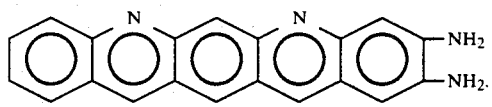

The purpose of the diamine is to react with and thereby reduce the level of biacetyl which is formed in the methyl methacrylate production process. The diamines complex with the biacetyl to form a high boiling compound which is removed from the process along with the used, spent, acid. Accordingly, the amount of diamine is adjusted in accordance with the concentration of biacetyl formed under the particular process conditions used. Typically, biacetyl may be present in a concentration of 2 to 10 parts per million. For removal of the biacetyl, a quantity of the diamine should preferably be added so as to provide about from 1 to 200 moles of diamine per mole of biacetyl. Little reduction of biacetyl is obtained with less than one mole of diamine per mole of biacetyl, and no significant additional benefit is realized with molar ratios in excess of 200. An excess of diamine is preferably used, however, since some diamine is deactivated by the acid solution. Preferably, at least about 20 moles of diamine are added per mole of biacetyl to be removed.

The level of biacetyl in methyl methacrylate can be determined through the use of an ultraviolet spectrophotometer capable of scanning from 400 nm to 600 nm. The methyl methacrylate is scanned over this range, in a 10 centimeter cell without dilution. The reasonably level base line in the 500–600 nm region is extrapolated to the 400 nm region, underneath the biacetyl peak of 418 nm. The biacetyl absorption is then determined by measuring the greatest peak height, in millimeters, of the broad biacetyl peak relative to the base line. This method separates out the biacetyl absorbants from other absorbers in the sample which can change the slope of the baseline.

The aromatic diamine is added in the presence of a strong acid catalyst, including, for example, sulfuric, hydrochloric, nitric and chlorosulfonic. In general, sulfuric acid will be present, since this acid is most typically used in the methyl methacrylate production process. The acid should comprise about from 0.1 to 65 percent by weight of the reaction mixture, and preferably at least about 0.2 weight percent. The aromatic diamine can be added at any point in the methyl methacrylate preparation. Preferably, the diamine is added prior to separation of the acid from the methyl methacrylate product, so that separate addition of the acid is not necessary. It has been found to be particularly convenient to add the diamine in the esterification reactor. However, if desired, the diamine can be added after separation of the finished monomer, with the addition of an appropriate quantity of mineral acid.

The addition of an excess of aromatic diamine in accordance with the instant invention results in the substantially complete removal of the biacetyl by-product. This, in turn, reduces or eliminates yellow color in sheet products made using the methyl methacrylate so produced. The yellowness in sheets of poly methyl methacrylate is most often noticed around the edges of the sheet material. The diamines of the present process, and the reaction products of diamine plus biacetyl, having high boiling points, are easily removed from the methyl methacrylate product with the spent acid, when the acid is removed for regeneration or disposal.

The present invention is further illustrated by the following specific examples, in which parts and percentages are by weight unless otherwise indicated.

EXAMPLE 1

Acetone cyanohydride was reacted with oleum containing about 1.8% excess sulfur trioxide in a series of three circulating water-cooled reactors, each having a residence time of 10 to 20 minutes. The ratio of oleum to acetone cyanohydrin in the feed to each reactor was adjusted to keep the reactor temperatures between 85° and 115° C. The final oleum to acetone cyanohydrin weight ratio was approximately 1.5. The intermediate product thus formed was heated at 135°–140° C. for 8–10 minutes for conversion to methacrylamide.

The methacrylamide was then contacted in an esterification train of five vessels, with about 0.45 parts by weight of water and about 0.36 parts by weight of methanol per part of methacrylamide, to form methyl methacrylate. The methyl methacrylate was distilled from the acid and water mixture, unreacted methanol removal by further distillation, and the wet methyl methacrylate further distilled in two stages to first remove the remaining traces of water and methanol, and then to separate the pure methyl methacrylate from high boiling impurities. Methyl methacrylate from the final refining column was analyzed and the biacetyl level determined to be 5 parts per million.

A 0.7% solution of ortho-phenylene diamine in methanol was added continuously to the first esterification vessel in an amount to give an 80 fold molar excess of ortho-phenylene diamine based on the 5 parts per million biacetyl in the refined methyl methacrylate product. Addition was continued for 30 hours, after which the biacetyl level in the refined methyl methacrylate was tested and found to be undetectable. The methyl methacrylate exhibited no color on visual examination.

EXAMPLE 2

If procedure of Example 1 is repeated, except that an equimolar amount of ortho-phenylene diamine based on the five parts per million of biacetyl is added, then, after 30 hours of addition, the level of biacetyl in the refined methyl methacrylate will be decreased by one-half.

We claim:

1. In the process for producing methyl methacrylate monomer by reacting acetone cyanohydrin with sulfuric acid to form methacrylamide and esterifying the methacrylamide with methanol to form methyl methacrylate, and wherein biacetyl is produced as a by-product, the improvement which comprises adding to the reaction mixture an effective amount of hydrazine or aromatic ortho-diamine in the presence of about from 0.1 to 65 weight percent of an acid catalyst.

2. A process of claim 1 wherein the aromatic diamine is ortho-phenylene diamine.

3. A process of claim 2 wherein the ortho-phenylene diamine is present in a concentration to provide a molar ratio of ortho-phenylene diamine to the biacetyl produced in the process of about 1:1 to 200:1.

4. A process of claim 3 wherein the molar ratio of ortho-phenylene diamine to biacetyl is at least about 20:1.

5. A process of claim 1 wherein the acid catalyst consists essentially of sulfuric acid.

6. A process of claim 5 wherein the sulfuric acid is present in a concentration of at least about 0.2% by weight.

7. A process of claim 1 wherein aromatic diamine is added to the reaction mixture in the course of the esterification reaction.

* * * * *